United States Patent
Keidar (10) Patent No.: US 7,001,383 B2
(45) Date of Patent: Feb. 21, 2006

(54) REAL-TIME MONITORING AND MAPPING OF ABLATION LESION FORMATION IN THE HEART

(75) Inventor: Yaron Keidar, Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 236 days.

(21) Appl. No.: 10/277,079

(22) Filed: Oct. 21, 2002

(65) Prior Publication Data

US 2004/0078036 A1 Apr. 22, 2004

(51) Int. Cl.
A61B 18/18 (2006.01)

(52) U.S. Cl. .................. 606/41; 607/122; 600/509

(58) Field of Classification Search .................. 606/41, 606/32–35, 42, 45–50; 600/374, 509, 515, 600/523; 607/122
See application file for complete search history.

(56) References Cited

U.S. PATENT DOCUMENTS

| | | | |
|---|---|---|---|
| 5,156,151 A * | 10/1992 | Imran ........................ 600/375 |
| 5,546,951 A | 8/1996 | Ben-Haim |
| 5,588,432 A | 12/1996 | Crowley |
| 5,657,755 A * | 8/1997 | Desai ........................ 600/374 |
| 5,722,402 A * | 3/1998 | Swanson et al. ............ 600/374 |
| 5,820,580 A * | 10/1998 | Edwards et al. ............. 604/22 |
| 5,964,753 A | 10/1999 | Edwards |
| 6,014,579 A | 1/2000 | Pomeranz et al. |
| 6,027,500 A | 2/2000 | Buckles et al. |
| 6,052,618 A * | 4/2000 | Dahlke et al. .............. 600/523 |
| 6,070,094 A | 5/2000 | Swanson et al. |
| 6,071,281 A * | 6/2000 | Burnside et al. ............ 606/41 |
| 6,095,150 A | 8/2000 | Panescu et al. |
| 6,179,833 B1 | 1/2001 | Taylor |
| 6,322,558 B1 | 11/2001 | Taylor et al. |
| 6,558,382 B1 * | 5/2003 | Jahns et al. .................. 606/41 |
| 6,633,773 B1 * | 10/2003 | Reisfeld ..................... 600/407 |
| 6,650,927 B1 * | 11/2003 | Keidar ....................... 600/424 |
| 6,679,269 B1 * | 1/2004 | Swanson .................... 128/898 |
| 2003/0078494 A1 | 4/2003 | Panescu et al. |
| 2003/0109871 A1 | 6/2003 | Johnson et al. |

FOREIGN PATENT DOCUMENTS

EP 1 182 619 A2 2/2002
WO WO 96/32885 A1 10/1996

OTHER PUBLICATIONS

European Search Report EP 03256602 dated Sep. 8, 2004.
Germain D. et al: "MR Monitoring of Laser-Induced Lesions of the Liver in Vivo in a Low-Field Open Magnet: Temperature Mapping and Lesion Size Prediction", Journal of Magnetic Resonance Imaging; Jan. 2001; pp. 42-49; vol. 13; Wiley-Liss, Inc.
Hong Cao et al: "Using Electrical Impedance to Predict Catheter-Endocardial Contact During RF Cardiac Ablation"; IEEE Transactions on Biomedical Engineering; Mar. 2002; pp. 247-253; vol. 49, No. 3; IEEE.
European Search Report EP 05250156 dated May 13, 2005.

* cited by examiner

Primary Examiner—Michael Peffley
(74) Attorney, Agent, or Firm—Louis J. Capezzuto (57) ABSTRACT

A method is provided for ablating tissue in a heart of a subject during an ablation procedure. The method includes applying a local treatment to the heart at a plurality of sites designated for ablation. At each respective site, a parameter is sensed that is indicative of a level of ablation at the site. The method preferably includes displaying a map of the heart, and designating, on the map, during the ablation procedure, indications of the respective levels of ablation at the sites, responsive to the respective sensed parameters.

86 Claims, 3 Drawing Sheets

REAL-TIME MONITORING AND MAPPING OF ABLATION LESION FORMATION IN THE HEART

FIELD OF THE INVENTION

The present invention relates generally to invasive methods for geometric and electrical mapping of the heart, and specifically to methods for real-time monitoring and mapping of lesions formed by an ablation procedure in the heart.

BACKGROUND OF THE INVENTION

Cardiac mapping is used to locate aberrant electrical pathways and currents within the heart, as well as to diagnose mechanical and other aspects of cardiac activity. Various methods and devices have been described for mapping the heart. Radiofrequency (RF) ablation is used to treat cardiac arrhythmia by ablating and killing cardiac tissue in order to create non-conducting lesions that disrupt the abnormal electrical pathway causing the arrhythmia.

U.S. Pat. Nos. 5,546,951 and 6,066,094 to Ben-Haim, and European Patent 0 776 176 to Ben-Haim et al., which are assigned to the assignee of the present patent application and are incorporated herein by reference, describe methods for sensing an electrical property of heart tissue, for example, local activation time, as a function of the precise location within the heart. The data are acquired with a catheter that has electrical and location sensors in its distal tip, and which is advanced into the heart. Techniques for sensing cardiac electrical activity are also described in U.S. Pat. No. 5,471,982 to Edwards et al., commonly-assigned U.S. Pat. Nos. 5,391,199 and 6,066,094 to Ben-Haim, U.S. Pat. No. 6,052,618 to Dahlke et al., and in PCT Patent Publications WO94/06349 and WO97/24981, which are incorporated herein by reference.

Methods for creating a map of the electrical activity of the heart based on these data are described in U.S. Pat. Nos. 6,226,542 and 6,301,496 to Reisfeld, which are assigned to the assignee of the present patent application and are incorporated herein by reference. As indicated in these patents, location and electrical activity is preferably initially measured on about 10 to about 20 points on the interior surface of the heart. These data points are then generally sufficient to generate a preliminary reconstruction or map of the cardiac surface to a satisfactory quality. The preliminary map is often combined with data taken at additional points in order to generate a more comprehensive map of the heart's electrical activity. In clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, which alters the propagation of the heart's electrical activity and restores normal heart rhythm. Methods for constructing a cardiac map of the heart are also disclosed in U.S. Pat. Nos. 5,391,199 and 6,285,898 to Ben-Haim, and in U.S. Pat. Nos. 6,368,285 and 6,385,476 to Osadchy et al., which are assigned to the assignee of the present patent application and are incorporated herein by reference.

Catheters containing position sensors may be used to determine the trajectory of points on the cardiac surface. These trajectories may be used to infer motion characteristics such as the contractility of the tissue. As disclosed in U.S. Pat. No. 5,738,096 to Ben-Haim, which is assigned to the assignee of the present application and which is incorporated herein by reference, maps depicting such motion characteristics may be constructed when the trajectory information is sampled at a sufficient number of points in the heart.

European Patent Application EP 1 125 549 and corresponding U.S. patent application Ser. No. 09/506,766 to Ben-Haim et al., which are assigned to the assignee of the present patent application and are incorporated herein by reference, describe techniques for rapidly generating an electrical map of a chamber of the heart. The catheter used for these techniques is described as comprising a contact electrode at the distal tip of the catheter and an array of non-contact electrodes on the shaft of the catheter near the distal end. The catheter also comprises at least one position sensor. Information from the non-contact electrodes and contact electrode is used for generating a geometric and electrical map of the cardiac chamber.

U.S. Pat. No. 5,848,972 to Triedman et al., which is incorporated herein by reference, describes a method for endocardial activation mapping using a multi-electrode catheter. A multi-electrode catheter is advanced into a chamber of the heart. Anteroposterior and lateral fluorograms are obtained to establish the position and orientation of each of the electrodes. Electrograms are recorded from each of the electrodes in contact with the cardiac surface relative to a temporal reference such as the onset of the P-wave in sinus rhythm from a body surface ECG. After the initial electrograms are recorded, the catheter is repositioned, and fluorograms and electrograms are once again recorded. An electrical map is then constructed from the above information.

U.S. Pat. No. 4,649,924 to Taccardi, which is incorporated herein by reference, describes a method for the detection of intracardiac electrical potential fields. The '924 patent is illustrative of non-contact methods that have been proposed to simultaneously acquire a large amount of cardiac electrical information. In the method of the '924 patent, a catheter having a distal end portion is provided with a series of sensor electrodes distributed over its surface and connected to insulated electrical conductors for connection to signal sensing and processing means. The size and shape of the end portion are such that the electrodes are spaced substantially away from the wall of the cardiac chamber. The method of the '924 patent is said to detect the intracardiac potential fields in only a single cardiac beat.

PCT application WO 99/06112 to Rudy, which is incorporated herein by reference, describes an electrophysiological cardiac mapping system and method based on a non-contact, non-expanded multi-electrode catheter. Electrograms are obtained with catheters having from 42 to 122 electrodes.

U.S. Pat. No. 5,297,549 to Beatty et al., which is incorporated herein by reference, describes a method and apparatus for mapping the electrical potential distribution of a heart chamber. An intra-cardiac multielectrode mapping catheter assembly is inserted into the heart. The mapping catheter assembly includes a multi-electrode array with an integral reference electrode, or, preferably, a companion reference catheter. In use, the electrodes are deployed in the form of a substantially spherical array. The electrode array is spatially referenced to a point on the endocardial surface by the reference electrode or by the reference catheter, which is brought into contact with the endocardial surface. Knowledge of the location of each of the electrode sites on the array, as well as a knowledge of the cardiac geometry is determined by impedance plethysmography.

U.S. Pat. Nos. 5,385,146 and 5,450,846 to Goldreyer, which are incorporated herein by reference, describe a catheter that is said to be useful for mapping electrophysiological activity within the heart. The catheter body has a distal tip which is adapted for delivery of a stimulating pulse for pacing the heart or for ablating tissue in contact with the tip. The catheter further comprises at least one pair of orthogonal electrodes to generate a difference signal indicative of the local cardiac electrical activity adjacent the orthogonal electrodes.

U.S. Pat. No. 5,662,108 to Budd et al., which is incorporated herein by reference, describes a process for measuring electrophysiological data in a heart chamber. The method involves, in part, positioning a set of active and passive electrodes in the heart; supplying current to the active electrodes, thereby generating an electric field in the heart chamber; and measuring this electric field at the passive electrode sites. In one of the described embodiments, the passive electrodes are contained in an array positioned on an inflatable balloon of a balloon catheter.

U.S. Pat. No. 6,226,543 to Gilboa et al., which is incorporated herein by reference, describes a method of recording and displaying in the context of an image a location of a point-of-interest in a body during an intra-body medical procedure. The method employs a catheter inserted into a portion of the body, and an imaging instrument for imaging the portion of the body. The point-of-interest is displayed in the context of the image generated by the imaging instrument.

U.S. Pat. No. 5,718,241 to Ben-Haim, U.S. Pat. No. 6,216,027 to Willis et al., U.S. Pat. No. 6,004,269 to Crowley at al., and U.S. Pat. No. 5,769,846 to Edwards et al., which are incorporated herein by reference, describe techniques for directing a catheter to a desired treatment site in the heart and ablating tissue at the site. U.S. Pat. No. 6,353,751 to Swanson et al., which is incorporated herein by reference, describes systems for guiding a movable electrode within an array of electrodes located within the body.

SUMMARY OF THE INVENTION

It is an object of some aspects of the present invention to provide improved apparatus and methods for geometric and electrical mapping of the heart.

It is also an object of some aspects of the present invention to provide improved apparatus and methods for treatment of cardiac arrhythmias, such as atrial fibrillation.

It is a further object of some aspects of the present invention to provide improved apparatus and methods that increase the accuracy of procedures for cardiac tissue ablation for treatment of cardiac arrhythmias.

It is yet a further object of some aspects of the present invention to provide apparatus and methods that increase the effectiveness of procedures for cardiac tissue ablation for treatment of cardiac arrhythmias.

It is still a further object of some aspects of the present invention to provide apparatus and methods that improve the accuracy of delivery of radio frequency (RF) energy for creating a discrete lesion that disrupts an abnormal electrical pathway associated with cardiac arrhythmia.

In preferred embodiments of the present invention, a real-time cardiac ablation mapping system comprises a catheter and a display monitor. The catheter preferably comprises a position sensor, a tip electrode, and one or more temperature sensors, all of which are preferably fixed at or near a distal tip of the catheter. The position sensor generates or receives signals used to determine the position and orientation of the catheter within a chamber of the heart of a subject. The tip electrode is preferably configured to apply electrical signals to the heart for ablating cardiac tissue, and is also preferably configured for diagnostic purposes, such as facilitating mapping of the heart. During a cardiac ablation procedure, the catheter is inserted into the cardiac chamber, and is used, during a plurality of cardiac cycles, to acquire and record position information and information about a power dose applied by the tip electrode during ablation, including power information and temperature information generated by the temperature sensors. Using the position and power dose information, a three-dimensional, preferably color-coded reconstruction of the ablation lesion is generated and displayed in real time on the monitor.

Advantageously, embodiments of the present invention enable a user of the system to visually determine, in real-time during a procedure, which areas of the surface of the cardiac chamber have been ablated and which areas require application or re-application of the ablating electrode. As a result, a more complete non-conducting lesion is typically formed, without unnecessary ablation of excess cardiac tissue.

In some preferred embodiments of the present invention, a geometric and electrical map of the cardiac chamber is acquired prior to beginning the ablation procedure. During the ablation procedure, the reconstruction of the ablation lesion (e.g., responsive to temperature data) is overlaid on the pre-acquired cardiac map in real time.

Preferably, the tip electrode comprises a monopolar electrode. In this case, the mapping system preferably further comprises a back-pad electrode or other large electrode to complete the electrical circuit created by the mapping system. The back-pad electrode is preferably positioned to be in contact with the skin of the back of the subject, adjacent to the heart during the procedure. The dose of applied ablation energy is preferably calculated responsive additionally to a measure of impedance between the tip electrode and the back-pad electrode. Alternatively, the tip electrode comprises a bipolar or multipolar electrode, in which case a measure of impedance between the poles of the electrode is preferably used.

In some preferred embodiments of the present invention, the mapping system additionally comprises a location system, an ablation power generator, a junction box, an electrocardiogram (ECG) recording and/or monitoring system, and a computer. The junction box preferably routes (a) conducting wires and temperature sensor signals from the catheter to the ablation power generator, (b) location sensor information to the location system, and (c) diagnostic electrode signals to the ECG monitor. The ECG monitor is preferably coupled to receive signals from one or more body surface electrodes, so as to provide an ECG synchronization signal to the mapping system.

The location system preferably comprises a set of external radiators, the position sensor of the catheter, and a location system control unit. Optionally, the location system comprises additional position sensors fixed to the catheter.

The location system control unit receives signals from the position sensors, calculates the location of the sensors and the catheter, and transmits to the computer the location information and the energy dose information which relates to the location information.

The ablation power generator preferably generates power used by the tip electrode to perform ablation. The ablation power generator additionally measures one or more of the following: (a) the temperature of the temperature sensors, (b) power applied to the tissue of the cardiac chamber, and (c) the measure of impedance. The ablation power generator transmits this energy dose information to the location system control unit and/or the ECG monitor.

There is therefore provided, in accordance with a preferred embodiment of the present invention, a method for ablating tissue in a heart of a subject during an ablation procedure, including:

applying a local treatment to the heart at a plurality of sites designated for ablation;

sensing at each respective site a parameter that is indicative of a level of ablation at the site;

displaying a map of the heart; and designating, on the map, during the ablation procedure, indications of the respective levels of ablation at the sites, responsive to the respective sensed parameters.

Preferably, the method includes determining a location of each respective site, and designating the indications of the respective levels of ablation includes designating the indications of respective levels of ablation at the sites, responsive to the respective sensed parameters and to the respective determined locations.

For some applications, applying the local treatment includes applying a cryogenic source, a radioactive source, and/or a chemical to induce ablation. Preferably, each indication is translated into a color on a color scale.

Preferably, the map includes at least one of the following:

an electroanatomical activation map;

electroanatomical voltage amplitude map; or a map generated using a modality selected from the list consisting of: CT scanning, magnetic resonance imaging, fluoroscopy, echocardiography, single-photon computed tomography, and positron emission tomography.

Preferably, the method includes calculating a weighted average of levels of ablation at the site and at secondary sites in a vicinity of the site, wherein the weighting of each secondary site decreases as the distance of the secondary site from the site increases.

For some applications, the method includes segmenting a mapping volume including the sites into voxels, and designating the indications with respect to respective voxels of the mapping volume.

For some applications, the parameter includes a measure of electrical impedance at the site. Optionally, the method includes segmenting a surface area including the sites into planar segments, and designating the indications with respect to respective planar segments of the surface area. Alternatively, the surface area is segmented into triangular segments.

In some preferred embodiments, the local treatment is applied by applying energy to the heart. Examples of energy that can be applied include radiofrequency energy, energy generated by a laser, and ultrasound energy.

Preferably, sensing the parameter includes sensing a measure of the energy applied at the site. For some applications, sensing the parameter includes calculating a measure of a total amount of energy applied at the site.

In some preferred embodiments, sensing the parameter includes sensing a temperature of the site. For some applications, sensing the parameter includes determining a maximum temperature sensed at the site. Alternatively or additionally, sensing the parameter includes determining a maximal temperature time-gradient at the site.

There is also provided, in accordance with a preferred embodiment of the present invention, method for ablating tissue in an organ of a subject, including:

applying a local treatment to the organ at a plurality of sites designated for ablation;

sensing at each respective site a parameter that is indicative of a level of ablation at the site;

displaying a map of the organ; and designating, on the map, during the ablation procedure, indications of the respective levels of ablation at the sites, responsive to the respective sensed parameters.

In some preferred embodiments, the organ includes:

a liver of the subject;

a prostate of the subject; or a breast of the subject.

There is further provided, in accordance with a preferred embodiment of the present invention, apparatus for ablating tissue in a heart of a subject during an ablation procedure, including:

a probe, adapted to be inserted into the heart;

an ablation device, adapted to apply a local treatment to the heart so as to ablate tissue of the heart;

at least one sensor, adapted to sense a parameter that is indicative of a level of ablation;

a display monitor; and a computer, adapted to:

drive the ablation device to apply the local treatment to the heart at a plurality of sites designated for ablation, receive respective sensed parameters from the sensor, sensed when the sensor is located at or adjacent to the plurality of sites designated for ablation, display on the display monitor a map of the heart, and designate, on the map, during the ablation procedure, indications of the respective levels of ablation at the sites, responsive to the respective sensed parameters.

Preferably, the sensor is adapted to be fixed to the probe. For some applications, the probe includes a catheter. For some applications, the apparatus includes an ablation power generator, coupled to the ablation device, adapted to generate power for use by the ablation device for performing ablation.

In some preferred embodiments, the apparatus includes one or more body surface electrodes, adapted to be coupled to a surface of a body of the subject, and an electrocardiogram (ECG) monitor, adapted to receive signals from the body surface electrodes and to provide an ECG synchronization signal to the computer.

Preferably, the apparatus includes a position sensor, adapted to be fixed to the probe and to generate respective position sensor signals responsive to respective locations of the sites, and the computer is adapted to:

receive the respective position sensor signals and, responsive thereto, determine respective locations of the sites, when the position sensor is respectively located at or adjacent to the plurality of sites designated for ablation, and designate the indications of respective levels of ablation at the sites, responsive to the respective sensed parameters and to the respective determined locations.

For some applications, the sensor includes a temperature sensor. For some applications, the ablation device includes:

a laser;

an ultrasound transducer; and/or an ablation electrode, such as a monopolar or bipolar electrode, adapted to apply RF energy to the heart so as to ablate tissue of the heart.

When the ablation electrode includes a monopolar ablation electrode, preferably the apparatus includes a return electrode, adapted to be placed against skin of the subject and to complete an electrical circuit with the monopolar ablation electrode. For some applications, the sensor includes the ablation electrode, and the ablation electrode is adapted to sense the parameter indicative of the level of ablation.

For some applications, the sensor includes an energy sensor, adapted to sense a measure of the energy applied by the ablation device.

There is yet further provided, in accordance with a preferred embodiment of the present invention, apparatus for ablating tissue in an organ of a subject during an ablation procedure, including:

a probe, adapted to be inserted into the organ;

an ablation device, adapted to apply a local treatment to the organ so as to ablate tissue of the organ;

at least one sensor, adapted to sense a parameter that is indicative of a level of ablation;

a display monitor; and a computer, adapted to:

drive the ablation device to apply the local treatment to the organ at a plurality of sites designated for ablation, receive respective sensed parameters from the sensor, sensed when the sensor is located at or adjacent to the plurality of sites designated for ablation, display on the display monitor a map of the organ, and designate, on the map, during the ablation procedure, indications of the respective levels of ablation at the sites, responsive to the respective sensed parameters.

There is still further provided, in accordance with a preferred embodiment of the present invention, a computer software product for mapping an ablation procedure performed on tissue in a heart of a subject, the product including a computer-readable medium, in which program instructions are stored, which instructions, when read by a computer, cause the computer to:

receive a plurality of sensed parameters generated by a sensor, which senses the respective parameters when located at or adjacent to a plurality of sites designated for ablation, each sensed parameter being indicative of a level of ablation, and designate, on a map of the heart, during the ablation procedure, indications of the level of ablation at each respective site, responsive to the respective sensed parameters.

For some applications, the instructions cause the computer to cause an ablation device to apply a local treatment to the heart so as to ablate tissue of the heart. Preferably, the instructions cause the computer to display the map on a display monitor.

There is also provided, in accordance with a preferred embodiment of the present invention, a computer software product for mapping an ablation procedure performed on tissue in a organ of a subject, the product including a computer-readable medium, in which program instructions are stored, which instructions, when read by a computer, cause the computer to:

receive a plurality of sensed parameters generated by a sensor, which senses the respective parameters when located at or adjacent to a plurality of sites designated for ablation, each sensed parameter being indicative of a level of ablation, and designate, on a map of the organ, during the ablation procedure, indications of the level of ablation at each respective site, responsive to the respective sensed parameters.

There is also provided, in accordance with a preferred embodiment of the present invention, apparatus for ablating tissue in a heart of a subject during an ablation procedure, including:

a probe, adapted to be inserted into the heart;

an ablation device, adapted to apply a local treatment to the heart so as to ablate tissue of the heart;

at least one ablation sensor, adapted to be fixed to the probe and to sense a parameter that is indicative of a level of ablation;

a position sensor, adapted to be fixed to the probe and to generate position sensor signals;

a display monitor; and a computer, adapted to:

drive the ablation device to apply the local treatment to the heart at a plurality of sites designated for ablation, receive respective sensed parameters from the ablation sensor, sensed when the ablation sensor is located at or adjacent to the plurality of sites designated for ablation, receive respective position sensor signals from the position sensor and, responsive thereto, determine respective locations of the sites, when the position sensor is respectively located at or adjacent to the plurality of sites designated for ablation, display on the display monitor a map of the heart, and designate, on the map, during the ablation procedure, indications of the respective levels of ablation at the sites, responsive to the respective sensed parameters and to the respective determined locations.

The present invention will be more fully understood from the following detailed description of the preferred embodiments thereof, taken together with the drawings in which:

DETAILED DESCRIPTION OF PREFERRED EMBODIMENTS

Figure 1:
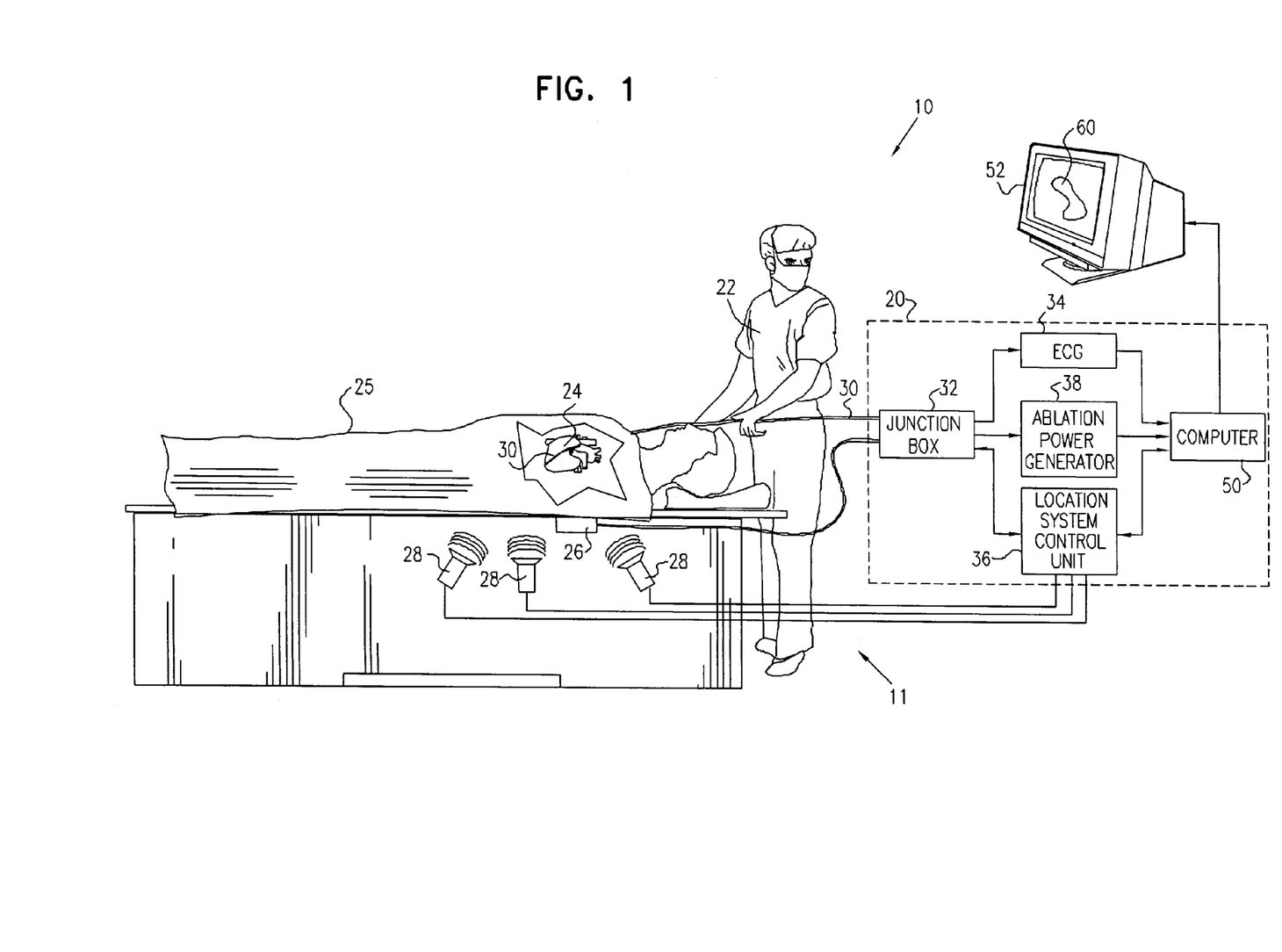
FIG. 1 is a schematic, pictorial illustration of a system for real-time mapping of cardiac ablation treatment in the heart, in accordance with a preferred embodiment of the present invention.

FIG. 1 is a schematic, pictorial illustration of a mapping system 10, for real-time mapping of cardiac ablation treatment in a heart 24 of a subject 25, in accordance with a preferred embodiment of the present invention. System 10 comprises an elongated mapping probe, preferably a catheter 30, which is inserted by a user 22 through a vein or artery of the subject into a chamber of the heart.

Figure 2:
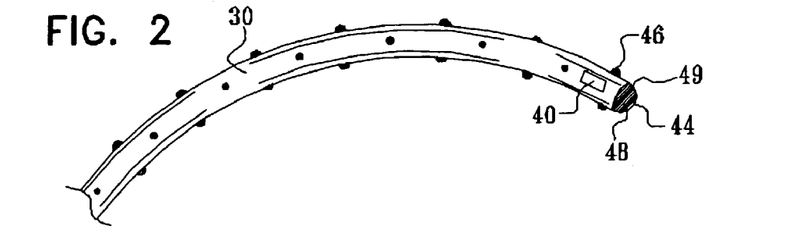
FIG. 2 is a schematic, pictorial illustration of a distal portion of a catheter used in the system of FIG. 1, in accordance with a preferred embodiment of the present invention.

FIG. 2 is a schematic, pictorial illustration showing a distal portion of catheter 30, which is inserted into heart 24. Catheter 30 preferably comprises at least one position sensor 40, a tip electrode 48, and one or more temperature sensors 49, all of which are preferably fixed at or near a distal tip 44 of the catheter. Temperature sensors 49 may comprise, for example, thermocouples and/or thermistors. Position sensor 40 generates or receives signals used to determine the position and orientation of catheter 40 within the chamber of the heart. Tip electrode 48 is preferably configured to apply electrical signals to heart 24 for ablating cardiac tissue, and is preferably further configured for diagnostic purposes such as cardiac mapping. Alternatively, separate electrodes are provided for diagnostic purposes and for ablating cardiac tissue. There is preferably a fixed positional and orientational relationship of position sensor 40, distal tip 44 and tip electrode 48. Optionally, catheter 30 further comprises at least one additional position sensor (not shown).

Suitable position sensors are described, for example, in the above-cited U.S. Pat. No. 5,391,199 to Ben-Haim, the above-cited European Patent 0 776 176 to Ben-Haim et al., co-pending U.S. patent application Ser. No. 10/029,473, filed Dec. 21, 2001, entitled, "Wireless position sensor," and/or in co-pending U.S. patent application Ser. No. 10/029,595, also filed Dec. 21, 2001, entitled, "Implantable and insertable tags," which are assigned to the assignee of the present patent application and are incorporated herein by reference. A preferred electromagnetic mapping sensor and system is manufactured by Biosense Webster (Israel) Ltd., (Tirat Hacarmel, Israel) and marketed under the trade designations NOGA™ and CARTO™. Alternatively or additionally, substantially any other suitable type of position/coordinate sensing device known in the art is used for position sensing. Still further alternatively or additionally, catheter 30 is marked with one or more markers whose positions can be determined from outside of the body. Suitable markers include radio-opaque markers to facilitate fluoroscopic measurements. Preferably, position sensing techniques are used that achieve continuous generation of up to six dimensions of location and orientation information with respect to sensors 40. "Position" information, as used in the context of the present patent application and in the claims, is to be understood as being indicative of the combination of location and orientation information, unless the context clearly indicates otherwise.

Reference is again made to FIG. 1. In a preferred embodiment of the present invention, mapping system 10 comprises a display monitor 52 and a console 20, which preferably comprises a location system control unit 36, an ablation power generator 38, a junction box 32, an electrocardiogram (ECG) recording and/or monitoring system 34, and a computer 50, which preferably comprises appropriate signal processing circuits that are typically contained inside a housing of the computer. Computer 50 is preferably programmed in software and/or hardware to carry out the functions described herein. This software may be downloaded to the computer in electronic form, over a network, for example, or it may alternatively be provided on tangible media, such as magnetic or optical media or other non-volatile memory. In some embodiments, computer 50 comprises a general-purpose computer.

Junction box 32 preferably routes (a) conducting wires and temperature sensor signals from catheter 30 to ablation power generator 38, (b) location sensor information from sensor 40 of catheter 30 to location system control unit 36, and (c) the diagnostic electrode signals generated by tip electrode 48 to ECG monitor 34. Alternatively or additionally, junction box 32 routes one or more of these signals directly to computer 50. ECG monitor 34 is preferably also coupled to receive signals from one or more body surface electrodes, so as to provide an ECG synchronization signal to computer 50.

A location system 11 preferably comprises a set of external radiators 28, position sensor 40 of catheter 30 and any additional position sensors, and location system control unit 36. External radiators 28 are preferably adapted to be located at respective positions external to subject 25 and to generate fields, such as electromagnetic fields, towards position sensor 40, which is adapted to detect the fields and facilitate a calculation of its position coordinates by location system control unit 36 responsive to the fields. Alternatively, position sensor 40 generates fields, which are detected by external radiators 28. For some applications, a reference position sensor, typically either on an externally-applied reference patch attached to the exterior of the body of the subject, or on an internally-placed catheter, is maintained in a generally fixed position relative to heart 24. By comparing the position of catheter 30 to that of the reference catheter, the coordinates of catheter 30 are accurately determined relative to the heart, irrespective of motion of the subject. Alternatively, any other suitable method may be used to compensate for such motion.

Location system control unit 36 receives signals from position sensor 40 (or from external radiators 28 when position sensor 40 generates the energy fields), calculates the location of sensor 40 and catheter 30, and transmits to computer 50 the location information and energy dose information (received from ablation power generator 38, as described below) which relates to the location information. The location system control unit preferably generates and transmits location information (a) essentially continuously, (b) between about one and 10 times per second, or (c) once per cardiac cycle.

Ablation power generator 38 preferably generates power used by tip electrode 48 to perform ablation. Preferably, the ablation power generator generates RF power for performing RF ablation. Alternatively or additionally, the ablation power generator induces ablation by means of other ablation techniques, such as laser ablation, cryogenic ablation, ultrasound ablation, radioactivity-induced ablation, or chemically-induced ablation. Preferably, suitable feedback techniques are applied to facilitate identifying ablated regions on the cardiac map.

Additionally, ablation power generator 38 measures one or more of the following: (a) the temperature of temperature sensors 49, (b) the power applied to the tissue of the cardiac chamber by tip electrode 48, and (c) a measure of impedance, as described below (together, the "energy dose information"). The ablation power generator transmits this energy dose information and preferably over a serial communications line, to location system control unit 36 and/or ECG monitor 34. Alternatively or additionally, the ablation power generator transmits some or all of this information directly to computer 50. The ablation power generator preferably measures and transmits the energy dose information (a) essentially continuously, (b) between about one and 10 times per second, or (c) once per cardiac cycle.

Preferably, tip electrode 48 comprises a monopolar electrode. In this case, mapping system 10 preferably further comprises a back-pad electrode 26 to complete the electrical circuit created by the mapping system. The back-pad electrode is preferably positioned to be in contact with the skin of the back of subject 25, adjacent to heart 24 during the procedure. The measure of impedance is preferably measured between tip electrode 48 and back-pad electrode 26. Alternatively, tip electrode 48 comprises a bipolar or multipolar electrode, in which case the measure of impedance is preferably measured between the poles of the electrode.

In a preferred embodiment of the present invention, prior to a cardiac ablation procedure, catheter 30 is inserted into the chamber of heart 24, and is used to acquire and record geometric and electrical information about the surface of the chamber of the heart. Preferably, position and electrical information is acquired at an easily-identifiable annotation point in time, over a number of cardiac cycles. A geometric and electrical map (an "electroanatomical activation map") based thereupon is generated, preferably using techniques described in the above-cited U.S. Pat. Nos. 6,226,542 and 6,301,496 to Reisfeld, European patent application EP 1 125 549 and corresponding U.S. patent application Ser. No. 09/506,766 to Ben-Haim et al., and/or co-pending U.S. patent application Ser. No. 09/598,862 to Govari, which are incorporated herein by reference, adapted for use with the techniques described herein. Preferably, but not necessarily, electrical signals from the electrodes are measured using techniques described in co-pending U.S. patent application Ser. No. 09/805,093, filed Mar. 13, 2001, entitled, "Apparatus and method for measuring a plurality of electrical signals from the body of a patient," which is assigned to the assignee of the present patent application and which is incorporated herein by reference. Alternatively or additionally, an electroanatomical voltage amplitude map is acquired.

Alternatively, a cardiac map generated during a previous cardiac procedure is used. Further alternatively, a cardiac map is acquired from another source, such as an imaging modality (e.g., fluoroscopy, MRI, echocardiography, CT, single-photon computed tomography (SPECT), or positron emission tomography (PET)), and the location of the catheter is visualized on this map. In this case, computer 50 marks the ablation lesion locations on this map. Alternatively, for some applications, a cardiac map is not acquired, in which case only a map of the ablation lesion is generated, as described below.

Figure 3:
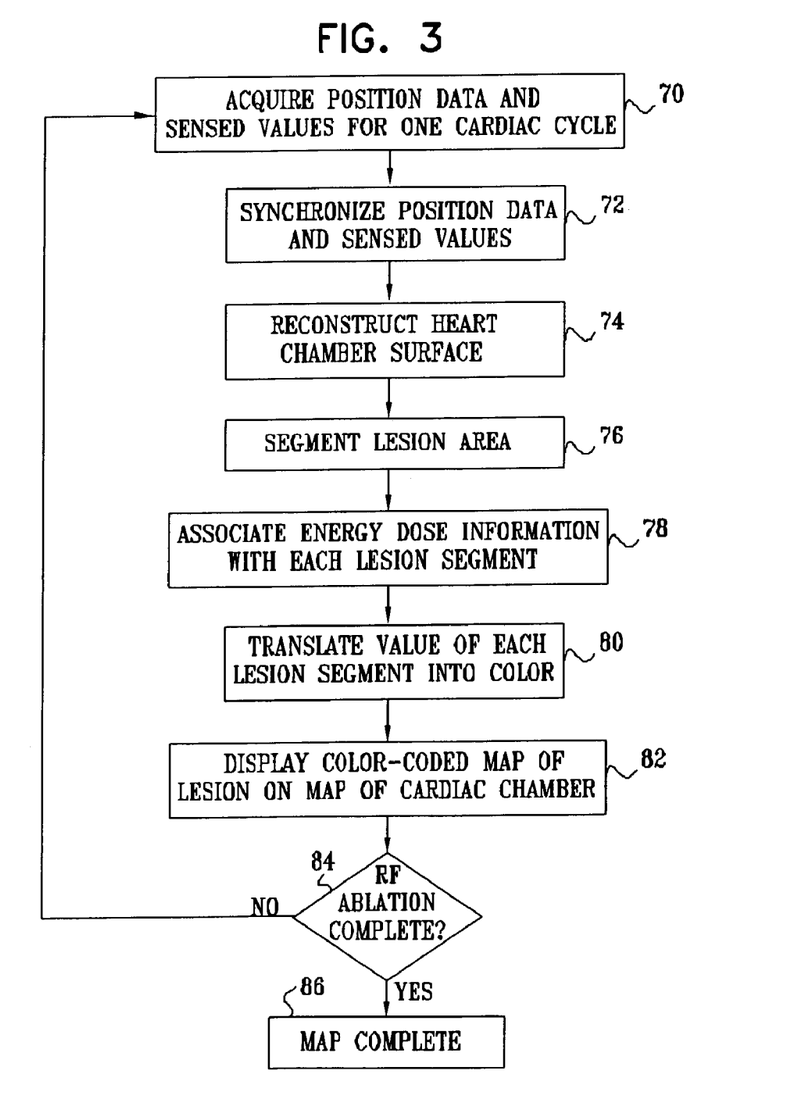
FIG. 3 is a flow chart that schematically illustrates a method for mapping a lesion formed in a cardiac chamber, in accordance with a preferred embodiment of the present invention.

FIG. 3 is a flow chart that schematically illustrates a method for mapping a lesion formed in a cardiac chamber, in accordance with a preferred embodiment of the present invention. After a geometric and electrical map of the cardiac chamber has been generated, as described above, user 22 advances catheter 30 to the area of the surface of the cardiac chamber on which ablation is to be performed. As ablation energy is applied to the cardiac surface, ablation power generator 38 measures, preferably continuously, the energy dose information, as described above. Preferably for each cardiac cycle, computer 50 receives (a) location information for the position of tip 44 of catheter 30 at the annotation point in the cardiac cycle and (b) energy dose information acquired during the cardiac cycle, at an acquisition and synchronization step 70. For each cardiac cycle during which ablation is performed, the computer uses the location information to calculate a three-dimensional ablation mapping point. The computer uses an ECG signal generated by ECG monitor 34 for synchronizing the location information with the energy dose information. For each cardiac cycle, the computer preferably associates the location of tip 44 at the annotation point with the series of measurements, at a synchronization step 72.

At a chamber reconstruction step 74, computer 50 generates a three-dimensional surface that connects the ablation mapping points generated at each iteration of step 70. Preferably, techniques described above with respect to generating a cardiac map are used. If a map of the cardiac surface was acquired prior to beginning ablation, these ablation mapping points are preferably added to this existing map. Preferably, the surface area of the ablation lesion reconstruction is segmented into small planar segments, preferably triangles, at a segmentation step 76. Preferably, these triangular segments have an average side length of about 3 millimeters, because such an area is generally large enough to contain at least one ablation mapping point.

Alternatively, the mapping volume is segmented into a grid of voxels, with each voxel segment preferably having dimensions of 2 millimeters by 2 millimeters by 2 millimeters.

Computer 50 generates display values for each segment, responsive to the energy dose information of the ablation mapping points within the segment, at a dose/segment association step 78. Preferably, user 22 selects one of several functions for the computer to use for generating the display values for each segment. Examples of such functions include:

Energy dose value: The energy dose value for a segment is calculated as the summation, over each measured energy dose i, of: (the measured energy dose i in the segment)*(the time interval between the measurement of dose i and the measurement of dose i−1)/(the area of the segment). (This area is typically constant when the segments are voxels.) At any given time, the display value of each segment represents the total energy delivered within the segment, as represented by the following equation:

$$E|_{segment} = \int P|_{segment} dt$$

where E represents energy in joules, P represents power in watts, and t represents time in seconds. Energy dose values for a 2 mm×2 mm×2 mm voxel segment are typically between 0 and 5,000 joules.

Maximum temperature: The average temperature for each ablation mapping point during each measurement period is calculated. At any given time, the display value of each segment equals the temperature of the hottest ablation mapping point measured in the segment during the ablation procedure. Temperature values are typically between 37 and 100 degrees Celsius.

Maximal temperature time-gradient: The temperature gradient for each ablation mapping point equals the slope of a linear regression performed on the temperature over time data for the ablation mapping point. The display value equals the highest value in the segment. Preferably, the display value is normalized by dividing it by the expected temperature gradient for the levels of temperature and power being used, based on empirical data. Temperature gradient values are typically between 0 and 20 degrees Celsius per second.

Average impedance: The display value equals the average impedance of the ablation mapping points in the segment. Impedance is generally a good indication of the quality of contact between tip electrode 48 and the tissue during ablation. Average impedance values are typically between 50 and 500 ohms.

Combination values: The display value is calculated as a combination of energy dose information and/or the above functions, such as, for example, energy multiplied by impedance or energy multiplied by maximum temperature.

In a preferred embodiment of the present invention, the segments comprise voxels, as described above, and a weighted display value is calculated for each segment. The weighted display value equals a weighted average of the display value of the segment and the display values of neighboring segments, with the weighting of each neighboring segment decreasing with distance from the segment. For example, the weighted display value for a segment may equal the sum of (a) the display value of the segment, (b) one half of the display values of once-removed segments, (c) one quarter of the display values of twice-removed segments, and (d) one eighth of the display values of thrice-removed segments, as shown in the following grid where x represents the display value of each of the segments:

| 1/8 × | 1/8 × | 1/8 × | 1/8 × | 1/8 × | 1/8 × | 1/8 × |
|---|---|---|---|---|---|---|
| 1/8 × | 1/4 × | 1/4 × | 1/4 × | 1/4 × | 1/4 × | 1/8 × |
| 1/8 × | 1/4 × | 1/2 × | 1/2 × | 112 × | 1/4 × | 1/8 × |
| 1/8 × | 1/4 × | 1/2 × | x | 1/2 × | 1/4 × | 1/8 × |
| 1/8 × | 1/4 × | 1/2 × | 1/2 × | 1/2 × | 1/4 × | 1/8 × |
| 1/8 × | 1/4 × | 1/4 × | 1/4 × | 1/4 × | 1/4 × | 1/8 × |
| 1/8 × | 1/8 × | 1/8 × | 1/8 × | 1/8 × | 1/8 × | 1/8 × |

The weighted display values are preferably normalized (in this example, preferably by dividing by 12). For some applications, the weighting is calculated in three dimensions. If the same weighting factors are used as in the preceding two-dimensional example, the weighted display values are preferably normalized by dividing the sum by 65.75. Preferably, weighting multipliers are determined based on empirical data regarding the actual thermal conduction of ablation energy and resulting ablation lesions in neighboring segments.

In this embodiment, the segments preferably comprise voxels with a relatively fine grid, such as 1 millimeter by 1 millimeter by 1 millimeter. This weighted-average approach is particularly useful when the display values are based on energy dose values, temperature values, and/or average impedance values, as described above. Advantageously, the application of a weighted average simulates thermal conduction that occurs in tissue.

Computer 50 translates the display value or weighted display value, as appropriate, of each segment into color using a color scale, at a color translation step 80. Computer 50 then displays on display monitor 52 the three-dimensional reconstruction of the ablation lesion with the segments colored based on their display values or weighted display values, at a map display step 82. Example color scales include a grayscale (ranging from black, representing the lowest value to progressively lighter shades of gray to white, representing the highest value) or a hot iron color scale (ranging from black, representing the lowest value, to blue to red to yellow to white, representing the highest value). Preferably, the colors of the color scale are not assigned pre-set ranges of display values. Rather, the ranges are preferably auto-scaled responsive to the total range of display values for a given ablation map. If a cardiac map was acquired prior to beginning ablation, the color-coded segments are preferably overlaid on this pre-acquired map and displayed together on display monitor 52. Advantageously, if user 22 determines that a particular site or region has not been sufficiently ablated, he can immediately return to the site and repeat the ablation procedure.

Computer 50 checks whether the ablation procedure is concluded, at a completion check step 84. If not, the steps of FIG. 3 are repeated for each cardiac cycle until the ablation procedure is concluded. If ablation has been concluded, then the computer ceases mapping, at a map completion step 86. As a result of the steps shown in FIG. 3, a real-time three-dimensional representation of the ablation lesion is generated for user 22 as the ablation procedure is being performed.

Figure 4:
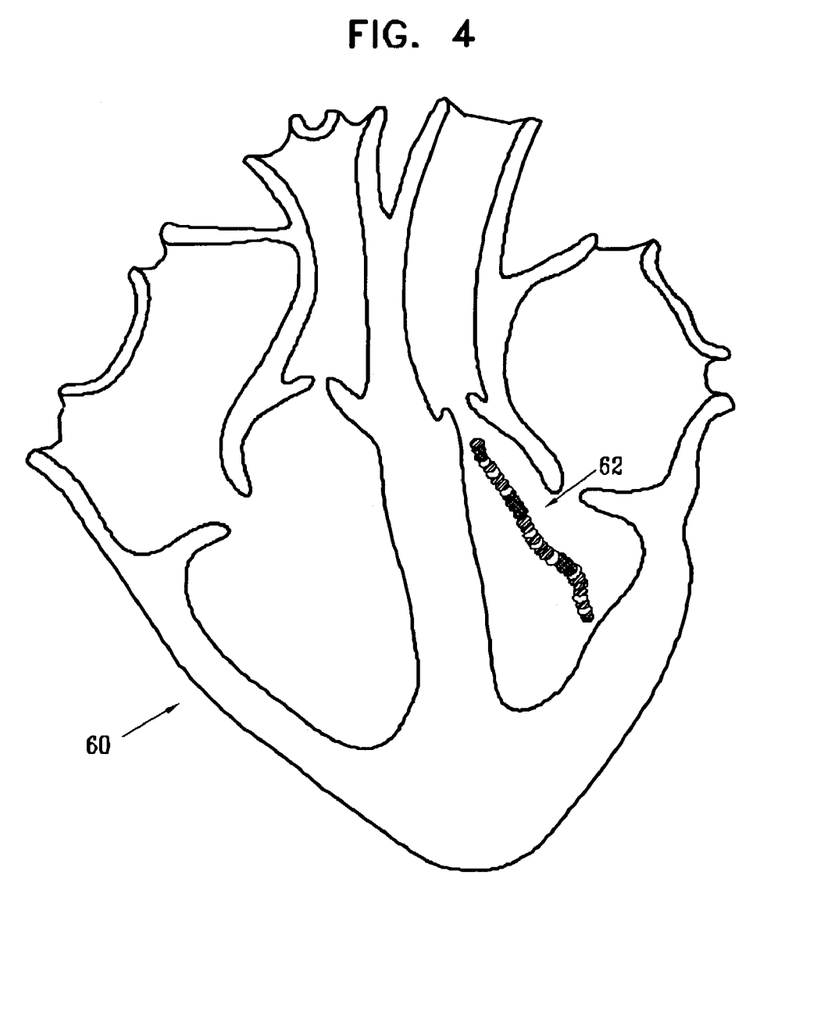
FIG. 4 is a schematic, pictorial representation of a highly-simplified black-and-white sample ablation lesion map, in accordance with a preferred embodiment of the present invention.

FIG. 4 is a schematic, pictorial representation of a sample, highly simplified black-and-white ablation lesion map 62 on a calculated or estimated map 60 of a cardiac chamber, in accordance with a preferred embodiment of the present invention. The various shadings of the plotted ablation mapping points of map 62 symbolically represent the color scale of the points. It will be appreciated that actual maps generated are preferably in color.

Although embodiments of the present invention have been described as being performed in a cardiac chamber, the techniques described herein can readily be applied to performing similar procedures in organs other than the heart and at other sites in the body.

Although some components of embodiments of the present invention are described herein and/or shown in the figures as being in one integral unit, such components may, alternatively, be housed in multiple discrete units. Likewise, components described and/or shown as discrete units may be integrated into one or more integral units.

It will thus be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for ablating tissue in a heart of a subject and mapping a level of ablation of the tissue during an ablation procedure, comprising:
    applying a local treatment to the heart at a plurality of sites designated for ablation;
    sensing at each respective site a parameter that is indicative of a level of ablation at the site;
    displaying a map of the heart;
    designating, on the map, during the ablation procedure, indications of the respective levels of ablation at the sites, responsive to the respective sensed parameters, and
    calculating a weighted average of levels of ablation at each respective site and at secondary sites in a vicinity of each respective site, such that the weighting of each secondary site decreases as the distance of the secondary site from each respective site increases.

2. A method according to claim 1, further comprising determining a location of each respective site, and designating on the map during the ablation procedure the indications of respective levels of ablation at the sites, responsive to the respective sensed parameters and the determined locations at the respective sites.

3. A method according to claim 1, wherein applying the local treatment comprises applying a cryogenic source to induce ablation.

4. A method according to claim 1, wherein applying the local treatment comprises applying a radioactive source to induce ablation.

5. A method according to claim 1, wherein applying the local treatment comprises applying a chemical to induce ablation.

6. A method according to claim 1, wherein designating the indications of the respective levels of ablation at the sites comprises translating each indication into a color on a color scale.

7. A method according to claim 1, wherein displaying the map comprises displaying an electroanatomical activation map.

8. A method according to claim 1, wherein displaying the map comprises displaying an electroanatomical voltage amplitude map.

9. A method according to claim 1, wherein displaying the map comprises displaying a map generated using a modality selected from the list consisting of: CT scanning, magnetic resonance imaging, fluoroscopy, echocardiography, single-photon computed tomography, and positron emission tomography.

10. A method according to claim 1, comprising segmenting a mapping volume including the sites into voxels, wherein designating the indications of the respective levels of ablation at the sites comprises designating the indications with respect to respective voxels of the mapping volume.

11. A method according to claim 1, wherein sensing the parameter comprises sensing a measure of electrical impedance at the site.

12. A method according to claim 1, comprising segmenting a surface area including the sites into planar segments, wherein designating the indications of the respective levels of ablation at the sites comprises designating the indications with respect to respective planar segments of the surface area.

13. A method according to claim 12, wherein segmenting the surface area comprises segmenting the surface area into triangular segments.

14. A method according to claim 1, wherein applying the local treatment comprises applying energy to the heart.

15. A method according to claim 14, wherein applying the energy comprises applying radiofrequency energy.

16. A method according to claim 14, wherein applying the energy comprises applying energy generated by a laser.

17. A method according to claim 14, wherein applying the energy comprises applying ultrasound energy.

18. A method according to claim 14, wherein sensing the parameter comprises sensing a measure of the energy applied at the site.

19. A method according to claim 18, wherein sensing the parameter comprises calculating a measure of a total amount of energy applied at the site.

20. A method according to claim 1, wherein sensing the parameter comprises sensing a temperature of the site.

21. A method according to claim 20, wherein sensing the parameter comprises determining a maximum temperature sensed at the site.

22. A method according to claim 20, wherein sensing the parameter comprises determining a maximal temperature time-gradient at the site.

23. A method for ablating tissue in an organ of a subject, and mapping a level of ablagtion of the tissue during an ablation procedure comprising:
   applying a local treatment to the organ at a plurality of sites designated for ablation;
   sensing at each respective site a parameter that is indicative of a level of ablation at the site;
   displaying a map of the organ;
   designating, on the map, during the ablation procedure, indications of the respective levels of ablation at the sites, responsive to the respective sensed parameters, and
   calculating a weighted average of levels of ablation at each respective site and at secondary sites in a vicinity of each respective site, such that the weighting of each secondary site decreases as the distance of the secondary site from each respective site increases.

24. A method according to claim 23, wherein the organ includes a liver of the subject, and wherein applying the local treatment comprises applying the treatment to the liver.

25. A method according to claim 23, wherein the organ includes a prostate of the subject, and wherein applying the local treatment comprises applying the treatment to the prostate.

26. A method according to claim 23, wherein the organ includes a breast of the subject, and wherein applying the local treatment comprises applying the treatment to the breast.

27. Apparatus for ablating tissue in a heart of a subject during an ablation procedure, comprising:
   a probe, adapted to be inserted into the heart;
   an ablation device, adapted to apply a local treatment to the heart so as to ablate tissue of the heart;
   at least one sensor, adapted to sense a parameter that is indicative of a level of ablation;
   a display monitor; and
   a computer, adapted to:
   drive the ablation device to apply the local treatment to the heart at a plurality of sites designated for ablation,
   receive respective sensed parameters from the sensor, sensed when the sensor is located at or adjacent to the plurality of sites designated for ablation,
   display on the display monitor a map of the heart,
   designate, on the map, during the ablation procedure, indications of the respective levels of ablation at the sites, responsive to the respective sensed parameters, and
   calculate a weighted average of levels of ablation at each respective site and at secondary sites in a vicinity of each respective site, such that the weighting of each secondary site decreases as the distance of the secondary site from each respective site increases.

28. Apparatus according to claim 27, wherein the sensor is adapted to be fixed to the probe.

29. Apparatus according to claim 27, wherein the probe comprises a catheter.

30. Apparatus according to claim 27, comprising an ablation power generator, coupled to the ablation device, adapted to generate power for use by the ablation device for performing ablation.

31. Apparatus according to claim 27, comprising one or more body surface electrodes, adapted to be coupled to a surface of a body of the subject, and an electrocardiogram (ECG) monitor, adapted to receive signals from the body surface electrodes and to provide an ECG synchronization signal to the computer.

32. Apparatus according to claim 27, comprising a position sensor, adapted to be fixed to the probe and to generate respective position sensor signals responsive to respective locations of the sites, wherein the computer is adapted to:
   receive the respective position sensor signals and, responsive thereto, determine respective locations of the sites, when the position sensor is respectively located at or adjacent to the plurality of sites designated for ablation, and
   designate the indications of respective levels of ablation at the sites, responsive to the respective sensed parameters and to the respective determined locations.

33. Apparatus according to claim 27, wherein the ablation device comprises a cryogenic element.

34. Apparatus according to claim 27, wherein the ablation device is adapted to apply radioactivity to induce ablation of the tissue.

35. Apparatus according to claim 27, wherein the ablation device comprises a chemical applicator, adapted to apply a chemical to induce ablation of the tissue.

36. Apparatus according to claim 27, wherein the computer is adapted to translate each indication into a color on a color scale, and to designate the translated indications on the map.

37. Apparatus according to claim 27, wherein the map comprises an electroanatomical activation map, and wherein the computer is adapted to display the electroanatomical activation map on the display monitor.

38. Apparatus according to claim 27, wherein the map comprises an electroanatomical voltage amplitude map, and wherein the computer is adapted to display the electroanatomical voltage amplitude map on the display monitor.

39. Apparatus according to claim 27, wherein the map comprises a map generated using a modality selected from the list consisting of: CT scanning, magnetic resonance imaging, fluoroscopy, echocardiography, single-photon computed tomography, and positron emission tomography, and wherein the computer is adapted to display the map on the display monitor.

40. Apparatus according to claim 27, wherein the computer is adapted to segment a mapping volume including the sites into voxels, and wherein the computer is adapted to designate, on the map, the indications of the respective levels of ablation at the sites with respect to respective voxels of the mapping volume.

41. Apparatus according to claim 27, wherein the parameter comprises a measure of electrical impedance, and wherein the sensor comprises an electrode, adapted to sense the measure of electrical impedance.

42. Apparatus according to claim 27, wherein the computer is adapted to segment a surface area including the sites into planar segments, and to designate the indications of the respective levels of ablation with respect to respective planar segments of the surface area.

43. Apparatus according to claim 42, wherein the computer is adapted to segment the surface area into triangular segments.

44. Apparatus according to claim 27, wherein the sensor comprises a temperature sensor.

45. Apparatus according to claim 44, wherein the computer is adapted to receive, from the temperature sensor, a sequence of sensed temperatures at one of the sites, and to determine responsive thereto a maximum temperature sensed at the site.

46. Apparatus according to claim 44, wherein the computer is adapted to receive, from the temperature sensor, a sequence of sensed temperatures at one of the sites, and to determine responsive thereto a maximal temperature time-gradient at the site.

47. Apparatus according to claim 27, wherein the ablation device is adapted to apply energy to the heart so as to ablate tissue of the heart.

48. Apparatus according to claim 47, wherein the ablation device comprises a laser.

49. Apparatus according to claim 47, wherein the ablation device comprises an ultrasound transducer, adapted to apply ultrasound energy to the heart so as to ablate tissue of the heart.

50. Apparatus according to claim 47, wherein the ablation device comprises an ablation electrode, adapted to apply RF energy to the heart so as to ablate tissue of the heart.

51. Apparatus according to claim 50, wherein the ablation electrode comprises a monopolar ablation electrode, and wherein the apparatus comprises a return electrode, adapted to be placed against skin of the subject and to complete an electrical circuit with the monopolar ablation electrode.

52. Apparatus according to claim 50, wherein the ablation electrode comprises a bipolar electrode.

53. Apparatus according to claim 50, wherein the sensor comprises the ablation electrode, and wherein the ablation electrode is adapted to sense the parameter indicative of the level of ablation.

54. Apparatus according to claim 47, wherein the sensor comprises an energy sensor, adapted to sense a measure of the energy applied by the ablation device.

55. Apparatus according to claim 54, wherein the computer is adapted to receive, from the sensor, respective sensed measures of energy applied at each of the sites, and to calculate for each site a measure of a total amount of energy applied.

56. Apparatus for ablating tissue in an organ of a subject during an ablation procedure, comprising:
   a probe, adapted to be inserted into the organ;
   an ablation device, adapted to apply a local treatment to the organ so as to ablate tissue of the organ;
   at least one sensor, adapted to sense a parameter that is indicative of a level of ablation;
   a display monitor; and
   a computer, adapted to:
   drive the ablation device to apply the local treatment to the organ at a plurality of sites designated for ablation,
   receive respective sensed parameters from the sensor, sensed when the sensor is located at or adjacent to the plurality of sites designated for ablation,
   display on the display monitor a map of the organ, and
   designate, on the map, during the ablation procedure, indications of the respective levels of ablation at the sites, responsive to the respective sensed parameters, and
   calculate a weighted average of levels of ablation at each respective site and at secondary sites in a vicinity of each respective site, such that the weighting of each secondary site decreases as the distance of the secondary site from each respective site increases.

57. Apparatus according to claim 56, wherein the organ includes a liver of the subject, and wherein the ablation device is adapted to apply the local treatment to the liver.

58. Apparatus according to claim 56, wherein the organ includes a prostate of the subject, and wherein the ablation device is adapted to apply the local treatment to the prostate.

59. Apparatus according to claim 56, wherein the organ includes a breast of the subject, and wherein the ablation device is adapted to apply the local treatment to the breast.

60. Apparatus for ablating tissue in a heart of a subject during an ablation procedure, comprising:
   a probe, adapted to be inserted into the heart;
   an ablation device, adapted to apply a local treatment to the heart so as to ablate tissue of the heart;
   at least one ablation sensor, adapted to be fixed to the probe and to sense a parameter that is indicative of a level of ablation;
   a position sensor, adapted to be fixed to the probe and to generate position sensor signals;
   a display monitor; and
   a computer, adapted to:
   drive the ablation device to apply the local treatment to the heart at a plurality of sites designated for ablation,
   receive respective sensed parameters from the ablation sensor, sensed when the ablation sensor is located at or adjacent to the plurality of sites designated for ablation,
   receive respective position sensor signals from the position sensor and, responsive thereto, determine respective locations of the sites, when the position sensor is respectively located at or adjacent to the plurality of sites designated for ablation, display on the display monitor a map of the heart, and designate, on the map, during the ablation procedure, indications of the respective levels of ablation at the sites, responsive to the respective sensed parameters and to the respective determined locations, and calculate a weighted average of levels of ablation at each respective site and at secondary sites in a vicinity of each respective site, such that the weighting of each secondary site decreases as the distance of the secondary site from each respective site increases.

61. Apparatus according to claim 60, wherein the probe comprises a catheter.

62. Apparatus according to claim 60, comprising an ablation power generator, coupled to the ablation device, adapted to generate power for use by the ablation device for performing ablation.

63. Apparatus according to claim 60, comprising one or more body surface electrodes, adapted to be coupled to a surface of a body of the subject, and an electrocardiogram (ECG) monitor, adapted to receive signals from the body surface electrodes and to provide an ECG synchronization signal to the computer.

64. Apparatus according to claim 60, wherein the ablation device comprises a cryogenic element.

65. Apparatus according to claim 60, wherein the ablation device is adapted to apply radioactivity to induce ablation of the tissue.

66. Apparatus according to claim 60, wherein the ablation device comprises a chemical applicator, adapted to apply a chemical to induce ablation of the tissue.

67. Apparatus according to claim 60, wherein the computer is adapted to translate each indication into a color on a color scale, and to designate the translated indications on the map.

68. Apparatus according to claim 60, wherein the map comprises an electroanatomical activation map, and wherein the computer is adapted to display the electroanatomical activation map on the display monitor.

69. Apparatus according to claim 60, wherein the map comprises an electroanatomical voltage amplitude map, and wherein the computer is adapted to display the electroanatomical voltage amplitude map on the display monitor.

70. Apparatus according to claim 60, wherein the map comprises a map generated using a modality selected from the list consisting of: CT scanning, magnetic resonance imaging, fluoroscopy, echocardiography, single-photon computed tomography, and positron emission tomography, and wherein the computer is adapted to display the map on the display monitor.

71. Apparatus according to claim 60, wherein the computer is adapted to segment a mapping volume including the sites into voxels, and wherein the computer is adapted to designate, on the map, the indications of the respective levels of ablation at the sites with respect to respective voxels of the mapping volume.

72. Apparatus according to claim 60, wherein the parameter comprises a measure of electrical impedance, and wherein the ablation sensor comprises an electrode, adapted to sense the measure of electrical impedance.

73. Apparatus according to claim 60, wherein the computer is adapted to segment a surface area including the sites into planar segments, and to designate the indications of the respective levels of ablation with respect to respective planar segments of the surface area.

74. Apparatus according to claim 73, wherein the computer is adapted to segment the surface area into triangular segments.

75. Apparatus according to claim 60, wherein the ablation sensor comprises a temperature sensor.

76. Apparatus according to claim 75, wherein the computer is adapted to receive, from the temperature sensor, a sequence of sensed temperatures at one of the sites, and to determine responsive thereto a maximum temperature sensed at the site.

77. Apparatus according to claim 75, wherein the computer is adapted to receive, from the temperature sensor, a sequence of sensed temperatures at one of the sites, and to determine responsive thereto a maximal temperature time-gradient at the site.

78. Apparatus according to claim 60, wherein the ablation device is adapted to apply energy to the heart so as to ablate tissue of the heart.

79. Apparatus according to claim 78, wherein the ablation device comprises a laser.

80. Apparatus according to claim 78, wherein the ablation device comprises an ultrasound transducer, adapted to apply ultrasound energy to the heart so as to ablate tissue of the heart.

81. Apparatus according to claim 78, wherein the ablation device comprises an ablation electrode, adapted to apply RF energy to the heart so as to ablate tissue of the heart.

82. Apparatus according to claim 81, wherein the ablation electrode comprises a monopolar ablation electrode, and wherein the apparatus comprises a return electrode, adapted to be placed against skin of the subject and to complete an electrical circuit with the monopolar ablation electrode.

83. Apparatus according to claim 81, wherein the ablation electrode comprises a bipolar electrode.

84. Apparatus according to claim 81, wherein the ablation sensor comprises the ablation electrode, and wherein the ablation electrode is adapted to sense the parameter indicative of the level of ablation.

85. Apparatus according to claim 78, wherein the ablation sensor comprises an energy sensor, adapted to sense a measure of the energy applied by the ablation device.

86. Apparatus according to claim 85, wherein the computer is adapted to receive, from the ablation sensor, respective sensed measures of energy applied at each of the sites, and to calculate for each site a measure of a total amount of energy applied.

\* \* \* \* \*